United States Patent [19]

Meyer et al.

[11] 4,438,259

[45] Mar. 20, 1984

[54] (VINYLARYL)ALKYL POLYSULFIDE POLYMERS

[75] Inventors: Victor E. Meyer; Thomas E. Dergazarian, both of Midland, Mich.

[73] Assignee: The Dow Chemical Company, Midland, Mich.

[21] Appl. No.: 426,559

[22] Filed: Sep. 29, 1982

Related U.S. Application Data

[63] Continuation-in-part of Ser. No. 339,820, Jan. 18, 1982, abandoned.

[51] Int. Cl.³ .............................................. C08G 75/00
[52] U.S. Cl. ................................... 528/388; 523/122; 523/265; 523/264; 568/23; 568/25; 568/38; 568/46; 568/50; 524/264; 524/265
[58] Field of Search ....................... 568/23, 25, 38, 46, 568/50; 528/388; 523/122; 524/264, 265

[56] References Cited

U.S. PATENT DOCUMENTS

| 1,890,101 | 12/1932 | Patrick | 528/388 |
| 2,445,191 | 7/1948 | Te Grotenhuis et al. | 528/388 |
| 2,631,994 | 3/1953 | Te Grotenhuis et al. | 528/388 |

OTHER PUBLICATIONS

Wulff et al., "Directed Cooperativity and Site Preparation of Mercapto Groups in Synthetic Polymers", Angew. Chem. Int. Ed. Eng. 17, (1978), No. 7, pp. 537–538.

Bordoloi et al., "Copolymerization of Liquid Sulfur with Certain Olefinic Systems and Structure–Property Studies on the Polymeric Materials", Journal of Polymer Science, Polymer Chemistry Ed., vol. 18, pp. 383–406, (1980).

Primary Examiner—Melvyn I. Marquis

[57] ABSTRACT

Di(vinylaryl)alkyl polysulfides and curable, low odor (vinylaryl)alkyl-terminated polysulfide copolymers having the general structure

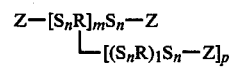

wherein n is an integer from about 2 to about 8, 1 and m are positive integers, each R is independently an organic polyradical with the radicals residing on carbon atoms, p is zero or a positive integer which is the difference between the number of radicals on R and 2, and each Z is independently chosen from the class consisting of (vinylaryl)alkyl and other noncrosslinking monoradicals, provided that a sufficient proportion of the Z groups are (vinylaryl)alkyl that the polymer, when cured, does not cold flow. Additionally, a method of preparing said polymers and useful adhesive, sealant and caulking compositions made therefrom are disclosed.

22 Claims, No Drawings

(VINYLARYL)ALKYL POLYSULFIDE POLYMERS

CROSS-REFERENCE TO RELATED APPLICATIONS

This application is a continuation-in-part of copending application Ser. No. 339,820, filed Jan. 18, 1982 and now abandoned.

BACKGROUND OF THE INVENTION

This invention relates to polysulfide polymers.

Polysulfide polymers are well-known and have been used commercially for many years. See, for example, U.S. Pat. Nos. 1,890,191 and 2,466,963. Such polysulfide polymers are prepared by copolymerizing metal polysulfides and polyfunctional aliphatic hydrocarbons such as ethylenedichloride, 1,2,3-trichloropropane and bis 2-chloroethyl formal. A very high molecular weight rubber is thereby formed, which is then cleaved with sodium hydrogen sulfide and sodium sulfite to yield a lower molecular weight mercaptan-terminated polymer. Although these mercaptan-terminated polymers may be cured by the use of oxidants such as metal oxides to form rubbers with many desirable properties, the mercaptan end groups of these polymers impart a strong, disagreeable odor which limits the practical utility of these polymers.

Grotenhuis et al. disclose in U.S. Pat. No. 2,445,191 that, in order to increase the resistance of polysulfides to cold flow, unsaturated aliphatic compounds may be incorporated into the copolymer such that there is one carbon-carbon double bond for each 100 to 300 carbon atoms. Grotenhuis further notes that a monosubstituted aliphatic compound may be employed to limit the molecular weight of the copolymers. However, the use of such copolymers has not proven commercially practical because said copolymers do not cure well.

Styrene is also known to react with sulfur to produce a high molecular weight polymer, but it rapidly depolymerizes to give 2,4-diphenylthiophene. See Blight et al., Adv. Chem. Ser. 165 13 (1978).

The copolymerization of bis(p-vinylbenzyl)disulfide with styrene and divinylbenzene to form a crosslinked polymer is reported by Wulff and Schulze in Angen Chem. Int. Ed. Engl. Vol. 17, pp. 537–80 (1978). The disulfide linkages are then reduced to mercaptan groups having a predetermined stereochemical relationship. Again, the presence of mercaptan groups imparts an undesirable odor to the crosslinked polymer, greatly limiting its utility.

In view of the deficiencies of previously known polysulfide resins, it is highly desirable to produce a curable polysulfide resin which is substantially free of offensive odors.

SUMMARY OF THE INVENTION

This invention is a curable polysulfide polymer which has little or no odor. Generally, the polymers of the present invention are polysulfide polymers having the general structure:

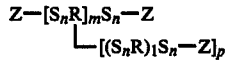

wherein each R is independently a polyvalent organic polyradical with each valence residing on a carbon atom; each Z is independently (vinylaryl)alkyl, inertly substituted (vinylaryl)alkyl or a noncrosslinking monoradical, provided that a sufficient proportion of Z contain a vinyl aryl moiety to enable the polymer to cure to a material that does not cold flow; l and m are independently zero or a positive integer; n is a number from about 2 to about 8 provided that when m is zero and each Z is vinylbenzyl then n is at least 3; and p is zero or a positive integer which is the difference between the valence of R and two.

In another aspect, this invention is a process by which curable polysulfide polymers are produced wherein desirable properties, i.e., molecular weight, curing properties and branching, are selectively imparted to the polymers. Said process comprises reacting a polysulfide salt of an alkali or alkaline earth metal with (vinylaryl)alkyl compound as described hereinafter and at least one inertly substituted polyfunctional organic compound having a plurality of negatively charged functionalities which will split off upon reacting with the metal polysulfide.

In yet another aspect, the present invention is a curable, water-resistant, polysulfide caulking composition and an adherent, polysulfide window sealing composition.

DETAILED DESCRIPTION OF THE INVENTION

The (vinylaryl)alkyl-terminated polysulfides of this invention are advantageously produced by the reaction of a metal polysulfide and a (vinylaryl)alkyl compound having negatively charged functionality which will split off upon reacting with the metal polysulfide. Metal polysulfides useful in the practice of this invention are soluble polysulfides of a mono- or divalent metal cation which forms a bond with the polysulfide which is primarily ionic in character, i.e. dissociates in water. Particularly useful metal polysulfides are those of calcium, magnesium, lithium, potassium and sodium. Of these, sodium polysulfides are most preferred on the basis of cost and availability.

Said metal polysulfides are prepared by reacting a dissolved metal monosulfide with elemental sulfur and refluxing the mixture to form the desired polysulfide. Alternately, the desired polysulfides are prepared by reacting anhydrous metal sulfides with molten sulfur or by reacting aqueous sodium hydroxide with elemental sulfur. See "Encyclopedia of Chemical Technology," 2d Ed., V. 16, page 255. The process by which the metal polysulfides are generated is a matter of choice to the practitioner of this invention, and should not be construed as critical to the practice of this invention.

The number of sulfur atoms in the polysulfide chain is referred to in the art as the sulfur "rank." The rank of the polysulfide chains is controlled by varying the proportions of the metal sulfide and elemental sulfur employed to form the metal polysulfide. By increasing the proportion of elemental sulfur to the metal sulfide, the average rank of the resulting polysulfide is increased. In the formation of the polysulfide by the reaction of NaOH with elemental sulfur, longer sulfur chains are formed by increasing the temperature at which the reaction is carried out. However, precise control of the sulfur rank is not achieved by any of these processes and the polysulfide chains so produced will have varying ranks. Thus, the "rank" of the sulfur chains produced represents only a number average of the actual individual ranks, and it is understood that said actual individual ranks will vary, usually between 2 to about 8, with the majority of the polysulfide chains having ranks within one of the designated rank. Thus, a polysulfide with a designated sulfur rank of 4 will have individual polysulfide chains having from 2 to about 8 sulfur atoms, with most of the polysulfide chains having 3, 4 or 5 sulfur atoms. In the polymers of this invention, the sulfur rank is in the range from about 2 to 8, with 2 to 4 being preferred.

In making the polysulfides of this invention, the metal polysulfide is reacted with a (vinylaryl)alkyl compound represented by the formula:

$$V-Ar-Y-X$$

wherein Ar is an unsubstituted or inertly substituted arylene group such as phenylene, naphthylene, phenanthrylene, biphenyl and the like, V is an unsubstituted or inertly substituted vinyl group, Y is an alkylene group and X is a negatively charged functionality which will split off upon reacting with the metal polysulfide in the reaction mixture. By inertly substituted is meant that the substituent group does not chemically react under the conditions of the polymerization reaction or the subsequent curing of the polymer. Exemplary inert substituents include alkyl groups or either the vinyl or arylene groups, or halogen substituents on the aromatic ring. Y may be a straight chain, cyclic or branched alkylene group, although straight chained groups having fewer than 8, preferably fewer than 5, most preferably 1, carbon atoms are preferred. More preferably, the (vinylaryl)alkyl compound is vinylbenzyl chloride, bromide or iodide, with the chloride being most preferred.

Polysulfide polymers are formed by introducing, in addition to the (vinylaryl)alkyl compound, an organic compound having a plurality of negatively charged functionalities attached to aliphatic or cycloaliphatic carbon esters which functionalities will split off upon reacting with the metal sulfide in the reaction mixture. As used herein, the term "negatively charged functionality" means a functional group which will split off on reacting with the metal polysulfide to form an anionic species in solution. The functional group is not necessarily ionically bonded to the aliphatic hydrocarbon or (vinylaryl)alkyl compound, and, in fact, is generally covalently bonded thereto. The polymerization of polysulfides and polyfunctional organic compounds are well known in the art and is first described in U.S. Pat. No. 1,890,191 to Patrick. Suitable polyfunctional compounds include alkyl dihalides, disulfates, diacetates and the like which will polymerize with the polysulfide and the (vinylaryl)alkyl compound to form a linear polymer represented by the formula:

$$V-Ar-Y-(S_nR_a)_mS_nY-Ar-V$$

wherein m is a positive integer, n, Ar, V and Y are as defined hereinbefore and $R_a$ represents an organic diradical, with each valence residing on a carbon atom, which is the residue of the difunctional hydrocarbon after the splitting off of the negatively charged functionalities. In general, chlorides are preferred as the negatively charged functional group due to the facility of their reaction with metal polysulfides, their relatively low cost and high availability. The R group, and correspondingly, the polyfunctional organic compound, may further contain substituents which are inert under the conditions of the polymerization reaction and may further incorporate linkages such as ether, sulfide, alkene or arylene into the chain. In general, those polyfunctional monomers previously known to react with metal polysulfides to form polymers therewith are also suitably employed in this invention. Preferred polyfunctional monomers include dichloroethane, 1,2,3-trichloropropane, bis-2-chloroethyl formal, bis-4-chlorobutyl ether, bis-4-chlorobutyl formal and 1,3-dichloro-2-propanol. Other polyfunctional monomers, which are illustrative of the wide scope of monomers suitably employed herein include, for example, bis(4-chloromethyl)phenyl ether, bis(4-chloroacetyl)phenyl ether, 2,5'-di(chloromethyl)1,4-dioxane and diethylene glycol bis(chloroacetate).

Trifunctional, tetrafunctional and pentafunctional organic compounds, such as 1,2,3-trichloropropane and the like, may be employed in conjunction with difunctional hydrocarbons and will polymerize with the polysulfide and the (vinylaryl)alkyl compound to form a branched polymer as represented by the general structure:

$$V-Ar-Y[S_nR]_mS_n-Z$$
$$\phantom{V-Ar-Y}\big|_{[(S_nR)_1S_n-Y-Ar-V]_p}$$

wherein l and m are positive integers, n, Ar, Y and V are as defined hereinbefore, each R is independently a polyvalent organic polyradical with each valence residing on a carbon atom, and p is zero or a positive number which is the difference between the valence of R and two. It is noted that each R is the residue formed by the splitting off of the negatively charged functionalities from the respective difunctional and polyfunctional hydrocarbons.

The amount and degree of branching of the polymer is selectively determined by the choice and relative proportion of the organic monomers employed in the reaction. By polymerizing polysulfides with a mixture of difunctional and tri-, tetra- or pentafunctional monomers, a branched chain may be formed as desired. In general, suitably branched polysulfide polymers are produced by employing from 90 to 99.5 weight percent of a difunctional monomer and from 10 to 0.5 weight percent of a monomer having at least three functionalities, said percentages being based on the total weight of all the polyfunctional monomers employed in the reaction. If high modulus and low cold flow in the cured polymer are desired, from about 2 to 10 weight percent, preferably from 3 to 5 weight percent, of a monomer having at least three functionalities is employed, said percentages being based on the total weight of all the polyfunctional monomers employed in the reaction. If the polymer is to be employed as a sealant, from about 0.5 to about 4 weight percent of a monomer having at least 3 functionalities is beneficially employed.

The polyfunctional monomer is chosen such that the polymer produced therefrom has the desired physical properties. Many of the beneficial properties of polysulfide polymers, such as resistance to oxygen permeation, water, ultraviolet light and solvents are generally attributable to the polysulfide segments of the polymer. By contrast, properties such as high elongation, flexibility, and increased solubility are selected to be imparted to the polymers primarily by the organic segments. Thus, the properties of the polymers of this invention can be selectively determined by the choice of organic monomers and the rank of the polysulfide segments. For example, a high sulfur polymer can be produced by employing low molecular weight organic compounds, such as bis-2-chloromethyl formal, 1,2,3-trichloropropane or ethylene dichloride. Similarly, polysulfides of varying rank may be employed to selectively vary the carbon to sulfur ratio in the polymeric chain.

The reaction is suitably carried out by heating the aqueous polysulfide solution from about 25° to about 90° C., preferably from about 50° to about 80° C., and adding the organic monomer and the (vinylaryl)alkyl compound over a period of about 5 minutes to 2 hours. The mixture is then heated at 25° to 90° C., preferably from about 50° to about 80° C., for about 1 to 3 hours to form the desired (vinylaryl)alkyl-terminated polysulfide.

Because the metal polysulfide is ordinarily contained in an aqueous phase, the organic reactants are advantageously intermixed with the aqueous phase to facilitate the reaction. Said intermixing may be is achieved by adjusting the density of the aqueous phase to approximate that of the organic phase or by forming an emulsion. An emulsion can be created by the addition of a suspending agent such as magnesium hydroxide in conjunction with a surfactant such as sodium lauryl sulfate or other organic surfactants such as alkylated sulfonated phenyl ethers. The suspended organic phase thus reacts more readily with the dissolved polysulfide to form the desired (vinylaryl)alkyl-terminated polysulfide. Following the reaction, the product is recovered by breaking the emulsion. This may be done by adding water and acid to adjust the pH to about 2 to 6, preferably from about 3 to 5. Alternatively, the product may be recovered by adding an organic solvent such as acetone, or by mechanical means such as centrifugation, or combinations thereof. Means for recovering organic products from an emulsion are well known in the art and are not considered critical to the invention. It may be preferred, for some applications, not to recover the polymer from the emulsion, but instead employ the polymer in the form of a latex.

By varying the proportion of the (vinylaryl)alkyl compound employed in the polymerization reaction, the molecular weight of the polymer is controlled. Molecular weight of the polymers formed according to this invention increases as the proportion of the (vinylaryl)alkyl compound is decreased. Thus, curable polymers of the desired molecular weight may be produced in a single reaction. The polymers of this invention have a theoretical molecular weight, as calculated from the relative proportions of the reactants employed, of at least about 490, preferably from about 3,000 to about 200,000, more preferably from about 5,000 to about 25,000. As molecular weight control in previously known processes for producing polysulfide resins cannot be achieved during the polymerization reaction, said control of the molecular weight represents a significant step forward in the art. In addition, control of the molecular weight in the polymerization reaction obviates the need for the cleavage step required in the formation of previously known polysulfide resins. Because the cleavage step in the prior art introduces terminal mercaptan groups to the resins thus produced, the elimination of this step produces a polymer free of the objectionable odors of previously known polysulfide resins.

The amount of crosslinking in the cured polymer is also controlled by the proportion of the (vinylaryl)alkyl compound employed in the polymerization reaction. While the precise mechanism of the curing reaction is not known, infrared studies indicate that curing is effected by cleavage of the polysulfide linkages, and subsequent reaction of the terminal sulfur radicals with the vinyl group in a rearrangement reaction to produce a highly crosslinked cured polymer. Thus, by reducing the amount of (vinylaryl)alkyl groups in the polymer, fewer crosslinks will be formed in the cured polymer. However, a sufficient proportion of the terminal groups of the polymer must be (vinylaryl)alkyl to enable the polymer to cure to a material that does not cold flow. By "cold flow" is meant that when the cured material is pressed onto a sheet of glass, said material will not flow under its own weight when the glass is held in a vertical position.

When a low molecular weight polymer which cures to form a lightly crosslinked resin is desired, a portion of the (vinylaryl)alkyl compound may be replaced with a noncrosslinking monofunctional organic compound having a single negatively charged functionality which splits off upon reacting with the metal polysulfide. Said noncrosslinking monofunctional organic compounds will become terminal groups of the polymers, thereby providing molecular weight control. However, because these monofunctional compounds are noncrosslinking, i.e., have no aliphatic carbon-carbon double bonds or other moieties which can cause crosslinking when the polymers are cured, reduced crosslinking in the cured resin can be achieved with coincident control of the molecular weight of the uncured resin. Substitution of a noncrosslinking monofunctional organic compound for a portion of the (vinylaryl)alkyl compound yields a polymer of the general form:

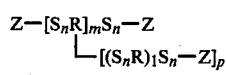

wherein l, m, n, R and Z are as defined hereinbefore provided that a significant proportion of Z are noncrosslinking. It is, of course, understood that the above structure represents only an average structure. Species having no (vinylaryl)alkyl terminal groups will probably form in this reaction, as well as species in which all terminal groups are (vinylaryl)alkyl, their relative proportions thereof being determined by the relative proportions and reactivity of the (vinylaryl)alkyl compound and the noncrosslinking monofunctional organic compound employed in the reaction mixture. It is preferred that the reactivity of the (vinylaryl)alkyl compound and the noncrosslinking monofunctional compound be roughly comparable. For this reason, benzyl chloride is highly preferred as the noncrosslinking monofunctional organic compound when vinylbenzyl chloride is employed as the (vinylaryl)alkyl compound. However, since the (vinylaryl)alkyl compound is essential for the curing of the polymers of this invention, a sufficient proportion of the terminal groups of the uncured polymers should be (vinylaryl)alkyl so that the cured polymer will be sufficiently crosslinked that the cured polymer does not cold flow. In general, at least 10 percent, by number, of the terminal groups of the uncured polymer should be (vinylaryl)alkyl.

Curing of the polysulfide polymers of this invention is readily effected by heating. Curing time is dependent on temperature; at 140° C. complete curing takes from about 10 to 30 minutes whereas curing at 240° C. requires about 1 to 10 minutes. Room temperature curing may be induced by combining the polysulfide polymer with such commonly known free-radical initiators as metal peroxides, organic peroxides, especially benzoyl peroxide and cumene hydroperoxide, or ultraviolet active curing agents such as the butyl ether of benzoin.

A surprising aspect of this invention is that room temperature curing is greatly enhanced if hydroxy functionalities are introduced into the polymer chain. Hydroxy functionalities are preferably introduced into the polymer chain by employing as one of the organic monomers a polyfunctional hydroxy-containing organic compound such as 1,3-dichlor-2-propanol. Significantly improved room-temperature curing is effected when about 1 to about 100 percent, by number, of the organic segments in the polymer contain at least one hydroxy group.

Because the properties of the polymers are readily controlled by varying the type and proportions of the reactants, the polymers of this invention are readily adapted to a wide variety of uses. Said polymers are useful coatings for materials such as wood, metal, glass, concrete and synthetic fibers as well as for absorbent materials such as textiles, paper, leather and the like. In addition, articles such as hoses, sheets, rollers, tanks, gaskets, wire insulation and the like may also be fashioned from said polymers. Said polymers are also useful as components in caulking and sealing compositions. Due to their low odor, the polymers of this invention may be used in household and other populated environments where the odor of previously known polysulfide polymers precludes their use.

Due to their good adhesion to glass and resistance to solvents, water and gases, the polymers of this invention have particular applications as sealants and in caulking compositions. Low modulus, highly extensible polysulfide polymers of this invention, i.e., those which are lightly branched and/or lightly crosslinked when cured, are most beneficially employed in sealant compositions. Plasticizers, fillers, pigments and the like may be beneficially employed in the sealant compositions according to this invention. Although the polymers of this invention adhere well to glass, adhesion is further increased by the incorporation of about 0.1 to about 5 weight percent of a coupling agent. Exemplary coupling agents include organosilane coupling agents such as mercaptopropyltrimethoxysilane and

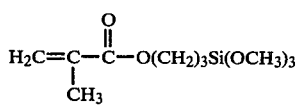

The sealants of the present invention exhibit excellent water and solvent resistance and gas impermeance.

Water-resistant caulking compositions are also prepared from the polymers of this invention. Polysulfide polymers of this invention which, when cured, exhibit high water-resistance, good adhesion, minimal cold flow and which cure relatively quickly at room temperatures are especially suitable for use in caulking compositions. In addition to their excellent mechanical properties, the polymers of this invention do not support fungal growth. For this reason, the polymers of this invention have an advantage over previously known caulking compositions, which must usually be compounded with a fungicide to inhibit fungal growth thereon.

To further extend the usefulness of the polymers of this invention, they may be compounded with various inert fillers such as fibers, wood flour, carbon black, asbestos, glass, inorganic pigments and the like.

The following examples are illustrative and are not intended to limit the scope of the invention in any way. All percentages are by weight unless specifically noted otherwise.

EXAMPLE 1

Preparation of Divinylbenzyltetrasulfide

A 96-g portion of hydrated disodium sulfide is dissolved into 100 g of water in a flask equipped with an agitator, a reflux condenser and a means for temperature control. A 37.5-g portion of precipitated sulfur is added and heated at reflux for 1 hour to produce a disodium polysulfide of average composition, $Na^+-SSSS-Na^+$. The mixture is then cooled to 70° C. and 8.5 g of hydrated magnesium chloride, 3.6 g of sodium hydroxide and 10 g of 30 percent sodium lauryl sulfate is added. While maintaining the reaction mixture at 70° C., 122 g of vinylbenzyl chloride (VBC) is added over a 1 hour period and followed by heating 1 hour at 70° C. One thousand milliliters of water and 10 ml of concentrated hydrochloric acid is then added to break the emulsion. An oily product is recovered which, after drying, weighs 76.6 g. Nuclear magnetic spectroscopy and infrared data reveal the structure of the product to be:

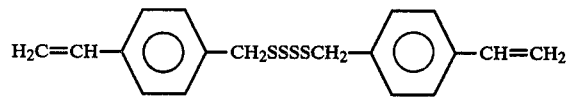

A 1.5 mil coating of the divinylbenzyl tetrasulfide thus obtained is coated onto a steel panel and baked at 200° C. for 10 minutes. A hard solvent resistant coating is thereby formed, which is rubbed with a cloth saturated with methyl ethyl ketone for 100 double rubs with no loss of gloss or removal of surface. Coating hardness is tested using a Kentron Model AK Micro Hardness tester with a 400 g loading. The baked coating exhibits a Knoop hardness of 32. The baked coating is tested for resistance to moisture by placing the coating into a humidity chamber at 150° C. for 24 hours. No visible effect is noted.

EXAMPLE 2

Preparation of Vinylbenzyl-Terminated Tetrasulfide/Ethylene Dichloride Polymers

Disodium tetrasulfide is prepared as in Example 1. The disodium tetrasulfide is heated to 70° C. and 8.5 g $MgCl_2.6 H_2O$, 3.6 g of sodium hydroxide and 10 g of 30 percent sodium lauryl sulfate is added to the mixture. Over a period of 1 hour, 30.5 g of VBC and 29.7 g of ethylene dichloride are added, followed by heating the mixture with agitation for 1½ hours. The emulsion is then broken by the addition of 1000 ml of water and 10 ml of glacial acetic acid. The recovered product (78 g) is a viscous oil insoluble in tetrahydrofuran, methyl ethyl ketone, methylchloroform and methyl chloride. Curing is effected by heating the product to 140° to 250° C.

Three grams of the product are mixed with 0.3 g of zinc oxide and 0.3 g of magnesium hydroxide and coated onto a steel panel. After heating at 140° C. for 30 minutes, a solid coating of 5 mil thickness is formed. A Gardner Impact tester is used to measure reverse impact durability using a two-pound weight in accordance with ASTM D-2794-69. The coating withstands an impact of 80 inch pounds with no coating failure as detected by a conductance test using a salt solution on the coating surface in the impact area. Resistance to methyl ethyl ketone is tested by subjecting the cured coating to 200 double rubs. No adverse effect is noted.

EXAMPLE 3

Preparation of Vinylbenzyl-Terminated Tetrasulfide/Ethylene Dichloride, 1,2,3-Trichloropropane Polymers Disodium tetrasulfide is prepared by heating a mixture of 216 g $Na_2S.9\,H_2O$, 87 g precipitated sulfur and 500 g water at reflux for one hour. The mixture is then cooled to 80° C. and 10 g NaOH, 8.5 g $MgCl_2.6\,H_2O$, 10.0 g of a 45 percent solution of a sodium salt of a dodecylated, sulfonated phenyl ether and 50.0 g water are added to form an emulsion. Over a period of one hour, 3.5 g of 1,2,3-trichloropropane, 93 g of ethylene dichloride and 6.0 g VBC are added, followed by a 1½ hour cook at 80° C.

The emulsion is broken by the addition of 2000 ml water and 10 ml glacial acetic acid. The recovered product is dried overnight at 50° C. under vacuum and a yield of 132.1 g of a lightly branched, low odor polymer is obtained.

The curing behavior of the polymer is measured by placing 8 g of the polymer into a Monsanto oscillating disc rheometer, heating to 140° C. and measuring the change in torque imparted by the polymer on the oscillating disc as a function of time. An increase in the torque is indicative of curing of the polymer. After 5 minutes at 140° C., the torque increases, indicating that curing has begun. After about 35 minutes, no futher increase in torque is seen, indicating that complete curing has occurred.

The glass adhesion properties of the polymer are tested in the following manner: A quantity of the polymer is mixed with 2.5 weight percent fumed silica, a thixotropic filler. This mixture is then divided into 4 parts, designated samples A, B, C and D. To samples B and D is added 2.5 weight percent of a mercaptopropyltrimethoxysilane coupling agent. Samples C and D are then further prepared for testing by forming 0.5 mil films thereof and curing said films by heating at 140° C. for about 30 minutes.

To test the glass adhesion of the prepared samples, 2 glass microscope slides are placed into a frame such that they are linearly aligned, with ⅛ inch overlap. A 0.5 mil coating of Sample A is coated onto the overlapped area of the slides such that an adhesive coating is formed between the sample and the glass slides. The slides thus coated are then heated to 140° C. for 30 minutes to cure the resin. The lap strength and percent elongation before failure is then measured by pulling the slides apart using an Instron tensile tester.

Sample B is tested in the same manner as Sample A.

Samples C and D are tested by placing a 0.5 mil film of the cured samples between 2 glass slides, and heating at 140° C. for 30 minutes to effect adhesion of the film to the slides. Lap strength and percent elongation are then tested as in Sample A.

For comparison, Sample O, a commercially available silicone sealant sold by the Dow Corning Corporation under the trade designation Dow Corning Silicone Rubber Sealant, is tested in the same manner as Sample A, except curing was effected by allowing to stand at room temperature for 24 hours.

The results of the various tests are given in Table A below.

TABLE A

| Sample | Lap Strength (1) (lb/in$^2$) | Elongation (2) % |
|---|---|---|
| A | 73 | 3 |
| B | 115 | 8 |
| C (3) | 82 | 3 |
| D (3) | 86 | 6 |
| O* | 80 | 5 |

*Not an example of this invention.
(1) Lap strength measured on an Instron Tensile Tester with the glass slides being pulled apart at the rate of 2 inches per minute. The lap strength is the maximum force applied to the slides before failure of the adhesive.
(2) Elongation is measured on an Instron Tensile Tester as the maximum distance the slides are pulled apart before failure of the adhesive.
(3) Precured for 30 minutes at 140° C.

It is seen from Table A that the sealants prepared in accordance with the present invention exhibit lap strength and elongation comparable to those of Comparative Sample O. Sample B, in particular, exhibits significantly improved adhesion and elongation. It is further seen that adequate adhesion and elongation are obtained when the sealants of this invention are cured in situ or when a precured sample is heat-adhered to the glass.

EXAMPLE 4

The reaction of Example 3 is repeated, this time substituting 1.0 g benzyl chloride and 5.0 g of VBC for the 6.0 g VBC employed in Example 3. The uncured resin has an extensibility of about 2000 percent as measured in an Instron tensile tester at a strain rate of 2 inches per minute. Curing of the polymer is effected in 15 minutes at 140° C. as measured by Monsanto rheometer. After curing, the resin has an extensibility of about 400 percent.

A caulking formulation is prepared by mixing 8.0 g of the above uncured resin, 1.6 g dioctylphthalate and 0.4 g fumed silica. An off-white caulk is obtained which is extensible to 1000 percent as measured in an Instron tensile tester at a strain rate of 2 inches per minute and does not cold flow when pressed onto glass and held in a vertical position.

EXAMPLE 5

The reaction of Example 3 is again repeated, this time using 2.0 g VBC and 6.0 g benzyl chloride instead of the VBC employed in Example 3. Upon testing in a Monsanto rheometer, no increase or maximum in the torque reading is noted upon heating to 140° C., indicating little or not curing. However, samples which are heated to 140° C. for several minutes are less tacky than samples which are not heated, and the samples which have been heated do not cold flow. The decreased tackiness and cold flow of the heated samples indicates that some curing does occur upon heating. These lightly cross-linked samples exhibit elongation to 1000 percent as measured in an Instron tensile tester at a strain rate of 2 inches per minute.

EXAMPLE 6

A quantity of disodium tetrasulfide is prepared as in Example 1, and maintaining the temperature at 70° C., 1.0 g of a sodium salt of a dodecylated, sulfonated phenyl ether surfactant, 3.6 g NaOH and 8.5 g $MgCl_2.6$ $H_2O$ are added. To this mixture are added 30.5 g VBC, 9.9 g ethylene dichloride and 25.8 g 1,3-dichloro-2-propanol. This mixture is then heated to 70° C. for one hour. The product is recovered by the addition of 1000 ml of water and 10 g of acetone, followed by drying overnight at 50° C. under vacuum. The product is a very viscous, rubbery oil having the general formula:

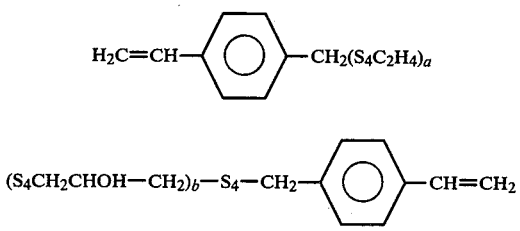

wherein a and b are positive integers with the ratio of a:b being approximately 1:2.

Three grams of the product are mixed with 0.3 g of 60 percent $CaO_2$, 3.0 g $TiO_2$ and 3.0 g methylene chloride. A 1 mil coating of this formulation is coated onto a glass slide. The coating is only slightly tacky after drying for 3 hours at room temperature and after 24 hours becomes a tack-free, enamel-like coating.

EXAMPLE 7

(Comparative)

The reaction of Example 6 is repeated, substituting 33.7 g of benzyl chloride for the VBC used in Example 6 and 34.4 g. 1,3-dichloro-2-propanol for the ethylene dichloride and the 1,3-dichloro-2-propanol employed in Example 7. The product is a very viscous, rubbery oil.

Three grams of this product is mixed with 0.3 g of 60 percent $CaCO_2$, 3.0 g $TiO_2$ and 3.0 g methylene chloride. In contrast with the formulation of Example 6, this polymer does not mix well with the $TiO_2$ and methylene chloride. A coating of this formulation is cast onto a glass slide, but no curing is noted upon standing at room temperature for 1 month, indicating that (vinylaryl)alkyl terminal groups are essential for curing to occur.

EXAMPLE 8

A quantity of disodium tetrasulfide is prepared as in Example 1. The disodium tetrasulfide mixture is cooled to 70° C. and an emulsion is formed by the addition of 5.0 g of a 45 percent solution of a sodium salt of a dodecylated sulfonated phenyl ether, 3.6 g NaOH and 8.5 g $MgCl_2.6$ $H_2O$. While maintaining the mixture at 70° C., 0.8 g VBC and 35.8 g ethylene dichloride is added over the period of 1 hour. The mixture is then heated at 70° C. for an additional hour, followed by the addition of 1000 ml of water and 10 g HCl to break the emulsion. An oily, rubbery product is recovered and dried under vacuum for 24 hours at 50° C.

The dried polymer is tested for resistance to fungal attack in the following manner: a 1 mm film of the polymer is cast onto a glass slide and cured at 140° C. for 30 minutes. Five 1-square centimeter samples of the film were removed from the glass slide and each was aseptically transferred to the surface of a mineral salts agar medium. Each sample was then inoculated with one of the following test organisms: (1) *Aspergillus niger* ATCC 9642, (2) *Aureobasidium pullulans* ATCC 9348, (3) *Chaetomium globosum* ATCC 6205, (4) *Penicillium funiculosum* ATCC 9644 and (5) *Trichoderma* sp. ATCC 9645. The cultures were incubated in the dark for 21 days at 30° C., and the growth of the fungi noted. The results of the tests are reported as Sample 8-A in Table B below.

For comparison, the above tests were repeated using, in place of the polymer film, sterile filter paper discs (Sample 8-B), a 1 cm × 1 cm × 1 mm film of a commercially available silicone sealant sold as Dow Corning Silicone Rubber Sealant, cured at room temperature for 24 hours (Sample 8-C), a 1 cm × 1 cm × 1 mm film of Dow Corning Silicone Rubber Bathtub Caulk, a commercial preparation containing a fungicide, cured at 27° C. for 24 hours (Sample 8-D) and Geocel ® 383, a commercial caulk available from Geocel Limited, Inc. (Sample 8-E). The results are as reported in Table B below.

TABLE B

| | Visible Growth of Test Organisms After 21 Days (1) | | | | |
|---|---|---|---|---|---|
| Sample | A. Niger | A. pullulans | C. globosum | P. funculosum | Trichoderma |
| 8-A | 0 | 0 | 0 | 0 | 0 |
| 8-B* | 4 | 4 | 4 | 4 | 4 |
| 8-C* | 0 | 1 | 1 | 0 | 1 |
| 8-D* | 0 | 0 | 0 | 0 | 0 |
| 8-E* | 0 | 1 | 0 | 0 | 0 |

*Not an example of this invention.
(1) The test material provides the sole source of carbon available for fungal growth. This test is a modification of ASTM G21-70. Ratings for visible growth of fungi recommended by ASTM:
No growth evident — Rating 0
Trace of growth evident — Rating 1
Light growth evident — Rating 2
Medium growth — Rating 3
Heavy growth — Rating 4

As can be seen from Table B, the cured polymer of this invention does not support any visible fungal growth. Of the other samples treated, only the commercial bathtub caulk containing a fungicide supports as little fungal growth as the present invention.

What is claimed is:

1. A curable polysulfide polymer as represented by the general structure

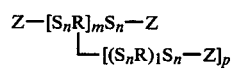

wherein each R is independently a polyvalent organic polyradical with each valence residing on a carbon atom; each Z is independently (vinylaryl)alkyl, inertly substituted (vinylaryl)alkyl or a noncrosslinking monoradical, provided that a sufficient proportion of Z contain a (vinylaryl)alkyl moiety to enable the polymer to cure to a material that does not cold flow; l and m are independently zero or a positive integer; n is a number from about 2 to about 8 provided that when m is zero and each Z is vinylbenzyl, then n is at least 3; and p is zero or a positive integer which is the difference between the valence of R and two.

2. A polymer as in claim 1 wherein m is zero, each Z is vinylbenzyl and n is a number from about 3 to about 8.

3. A polymer as in claim 1 wherein m is a positive integer.

4. A polymer as in claim 1 wherein each Z is (vinylaryl)alkyl.

5. A polymer as in claim 4 wherein each Z is vinylbenzyl.

6. A polymer as in claim 1 wherein each Z is vinylbenzyl or benzyl.

7. A polymer as in claim 1 wherein each R is independently an aliphatic diradical.

8. A polymer as in claim 1 wherein each R is independently an alkylene diradical, bis(4-chloromethyl)phenyl ether, bis-(4-chloroacetyl)phenyl ether, 2,5-di(chloromethyl)-1,4,-dioxane or diethylene glycol bis(chloroacetate).

9. A polymer as in claim 1 wherein each R is selected such that from about 90 to about 99.5 weight percent, based on the combined weight of all the R groups, of the R groups are organic diradicals and from about 10 to about 0.5 weight percent of the R groups have at least 3 valences.

10. A polymer as in claim 1 having a molecular weight from about 3,000 to 100,000.

11. A polymer as in claim 10 having a molecular weight from about 5,000 to 25,000.

12. A polymer as in claim 1 wherein from about 1 to about 100 percent, by number, of the R groups contain at least one hydroxy group.

13. A process for making polysulfide polymers, comprising reacting a mixture comprising an alkali or alkaline earth polysulfide, at least one unsubstituted or inertly substituted polyfunctional organic compound having a plurality of negatively charged functionalities attached to an aliphatic or alicyclic carbon atom, which functionalities will split off upon reacting with said alkali or alkaline earth polysulfide, and a (vinylaryl)alkyl compound having negatively charged functionality which will split off upon reacting with said alkali or alkaline earth polysulfide.

14. A process as in claim 13 wherein the reaction mixture further comprises a monofunctional noncrosslinking organic compound having a negatively charged functionality which will split off upon reacting with said alkali or alkaline earth polysulfide, such that a sufficient proportion of the terminal groups of the polymer so made are (vinylaryl)alkyl that the polymer, when cured, does not cold flow.

15. A process as in claim 13 or 14 wherein the reaction is carried out at a temperature from about 25° C. to about 90° C.

16. A process as in claim 13 or 14 wherein the reaction is carried out in an emulsion.

17. A polymer as in claim 1 in a sealant composition.

18. A sealant composition as in claim 17 further comprising a coupling agent.

19. A sealant composition as in claim 18 wherein said coupling agent is an organosilane coupling agent.

20. A polymer as in claim 1 in a caulking composition.

21. A polymer as in claim 1 in an adhesive composition.

22. A cured resin formed by curing the polymers of claim 1 or 2.

* * * * *